United States Patent [19]

Shapiro

[11] Patent Number: 5,052,372
[45] Date of Patent: Oct. 1, 1991

[54] VAGINAL SPECULUM HAVING A UNIQUE SINGLE CONTROL

[76] Inventor: Jerome J. Shapiro, Rte. 1, Box 302, Goldvein, Va. 22720

[21] Appl. No.: 411,270

[22] Filed: Sep. 25, 1989

Related U.S. Application Data

[63] Continuation of Ser. No. 179,482, Apr. 5, 1988, abandoned.

[51] Int. Cl.⁵ ............................................. A61B 1/32
[52] U.S. Cl. .................................................... 128/17
[58] Field of Search ...................... 128/17, 18, 20, 19, 128/3, 5; 606/193, 197, 198

[56] References Cited

U.S. PATENT DOCUMENTS

| | | | |
|---|---|---|---|
| 281,880 | 7/1893 | Hubbell | 128/17 |
| 977,489 | 12/1910 | Von Uhruh | 128/17 |
| 1,194,319 | 8/1917 | Pretts | 128/17 |
| 1,300,756 | 4/1919 | Moyer | 128/17 |
| 2,483,233 | 9/1949 | Price et al. | 128/345 |
| 3,040,738 | 6/1962 | Moore | 128/17 |
| 3,744,481 | 7/1973 | McDonald | 128/17 |
| 3,762,400 | 10/1973 | McDonald | 128/17 |
| 3,769,968 | 11/1973 | Blount et al. | 128/17 |
| 3,890,961 | 6/1975 | Moore et al. | 128/17 |

FOREIGN PATENT DOCUMENTS

| | | | |
|---|---|---|---|
| 113829 | 10/1876 | France | 128/17 |
| 1328110 | 8/1973 | United Kingdom | 128/17 |

*Primary Examiner*—Edward M. Coven
*Assistant Examiner*—Mark S. Graham
*Attorney, Agent, or Firm*—Shapiro and Shapiro

[57] ABSTRACT

A speculum for vaginal examination incorporates pin-and-slot connections between the upper and lower blades to enable individual or simultaneous adjustment of speculum aperture and blade angulation by simple application of thumb pressure on the upper blade handle. Small hinge pins on each side of the lower blade handle are pivotably and slidably received within corresponding slots on opposite sides of the upper blade handle. A single covering nut threaded on preferably the right-hand side hinge pin controls locking and releasing of the blades relative to one another for both phases of adjustment. Loosening the covering nut releases the blades for adjustment of angulation and/or aperture as desired, whereas tightening of the nut locks the blades in the desired configuration.

8 Claims, 4 Drawing Sheets

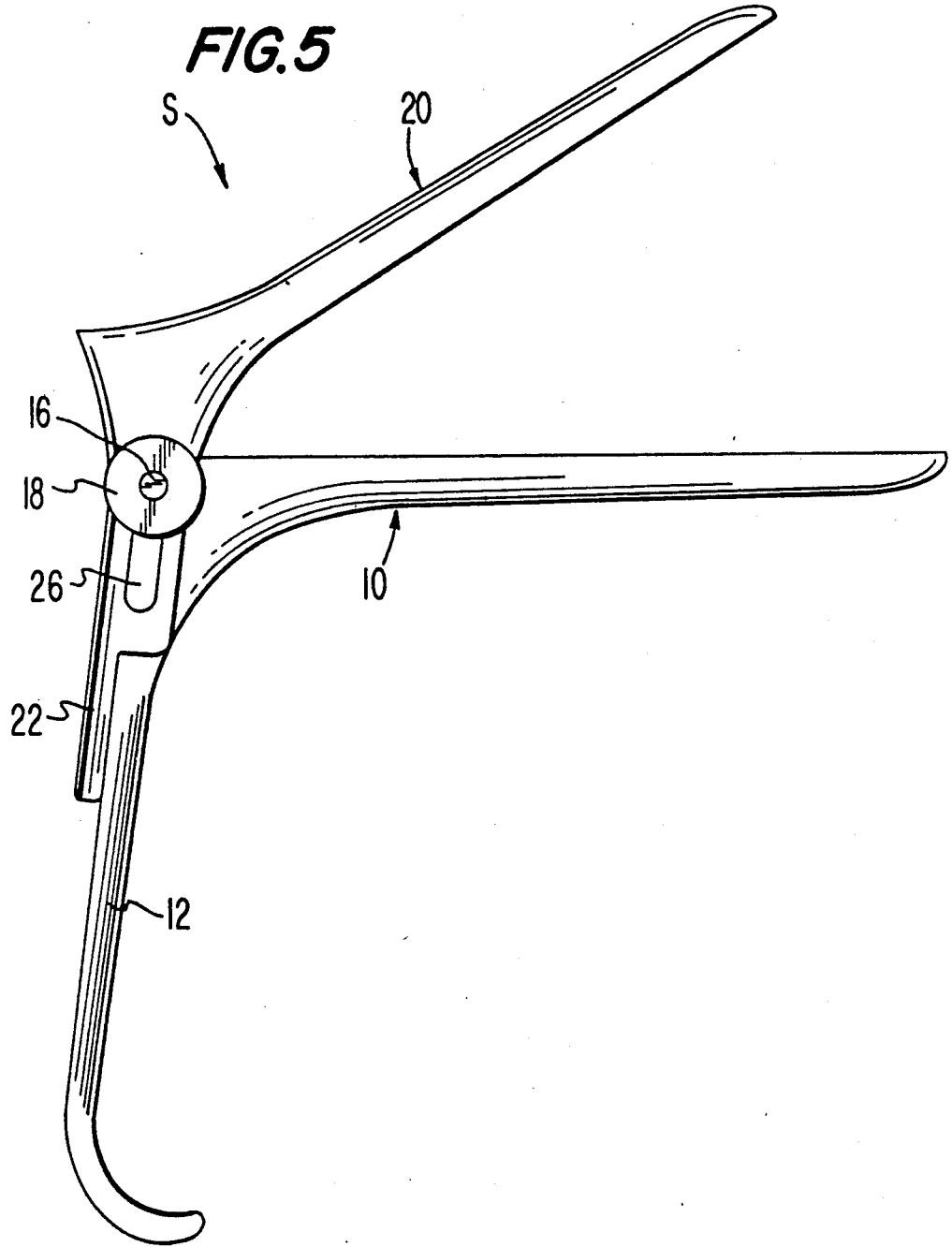

VAGINAL SPECULUM HAVING A UNIQUE SINGLE CONTROL

This is a continuation of application Ser. No. 179,482, filed Apr. 5, 1988, now abandoned.

BACKGROUND OF THE INVENTION

This invention relates to vaginal speculums, and is more particularly concerned with an improved speculum having a single control arrangement which enables the physician to release the blades for adjustment of blade aperture (speculum aperture) and/or blade angulation, as desired, simply by loosening a single covering nut, and thereafter to lock the blades at the adjusted aperture and angulation simply by tightening the covering nut. No speculum presently available offers the simplicity and ease of manipulation achieved by this arrangement.

Present state-of-the-art metal speculums have a slot in the upper blade handle which permits variation of the speculum aperture. A first covering nut must be loosened for aperture adjustment and then tightened to maintain the blades at the selected aperture. Blade angulation is adjusted with a thumb lever having a second covering nut. Angulation is increased by pushing down on the thumb lever and then fixed by tightening the second covering nut. At maximum angulation, the second covering nut must be threaded down a full inch in order to maintain the adjusted state. Operation of the two controls is required for both insertion and removal of the speculum, and this is quite tedious for the physician. The operation is even more tedious when a relaxation of the vagina is present.

A plastic speculum is presently available which allows control of blade angulation by a serrated projection selectively cooperable with lower and upper transverse slots in the lower blade handle. To obtain maximum aperture, the projection must be freed from the lower slot, and the upper blade handle then pushed upward to engage the projection in the upper slot. A major disadvantage of this speculum is that the blades can be secured at only maximum or minimum aperture; nothing between is possible. A second major disadvantage is the difficult manipulation required to change from maximum back to minimum aperture. In order to make this adjustment, the serrated projection must be freed from the upper transverse slot, and the upper blade then grasped and moved in a curved pattern back to the minimum aperture or "closed" position of the blades.

SUMMARY OF THE INVENTION

The present invention provides a novel speculum construction having only a single control for releasing and locking the blades and which permits the adjustment of both blade aperture (i.e., speculum aperture) and blade angulation by a simple application of thumb pressure to a thumb rest of the upper blade. The invention is thus easier and faster to use than such state-of-the-art speculums as were described above, thus simplifying the examination procedure and enhancing patient comfort.

More particularly, in one of its broad aspects, the invention provides a vaginal speculum comprising an upper blade and a lower blade adapted for insertion into the vagina and having respective depending rear handle portions to enable holding and manipulation of the blades by a physician, a rear portion of said lower blade having a pair of hinge pins respectively projecting outwardly from opposite sides thereof and received in corresponding slots in opposite sides of the handle portion of the upper blade, such that the handle portion of the upper blade may pivot on the hinge pins to adjust the angulation of the blades and may slide along the hinge pins to adjust the aperture of the blades, and a covering nut threaded to one of the hinge pins for locking the blades at the adjusted angulation and aperture.

BRIEF DESCRIPTION OF THE DRAWINGS

The invention will be better understood from the following detailed description, taken in conjunction with the accompanying drawings in which:

FIG. 5 is a right side view of the speculum with the blades at maximum angulation at the minimum aperture;

DETAILED DESCRIPTION OF THE INVENTION

Figure 1:
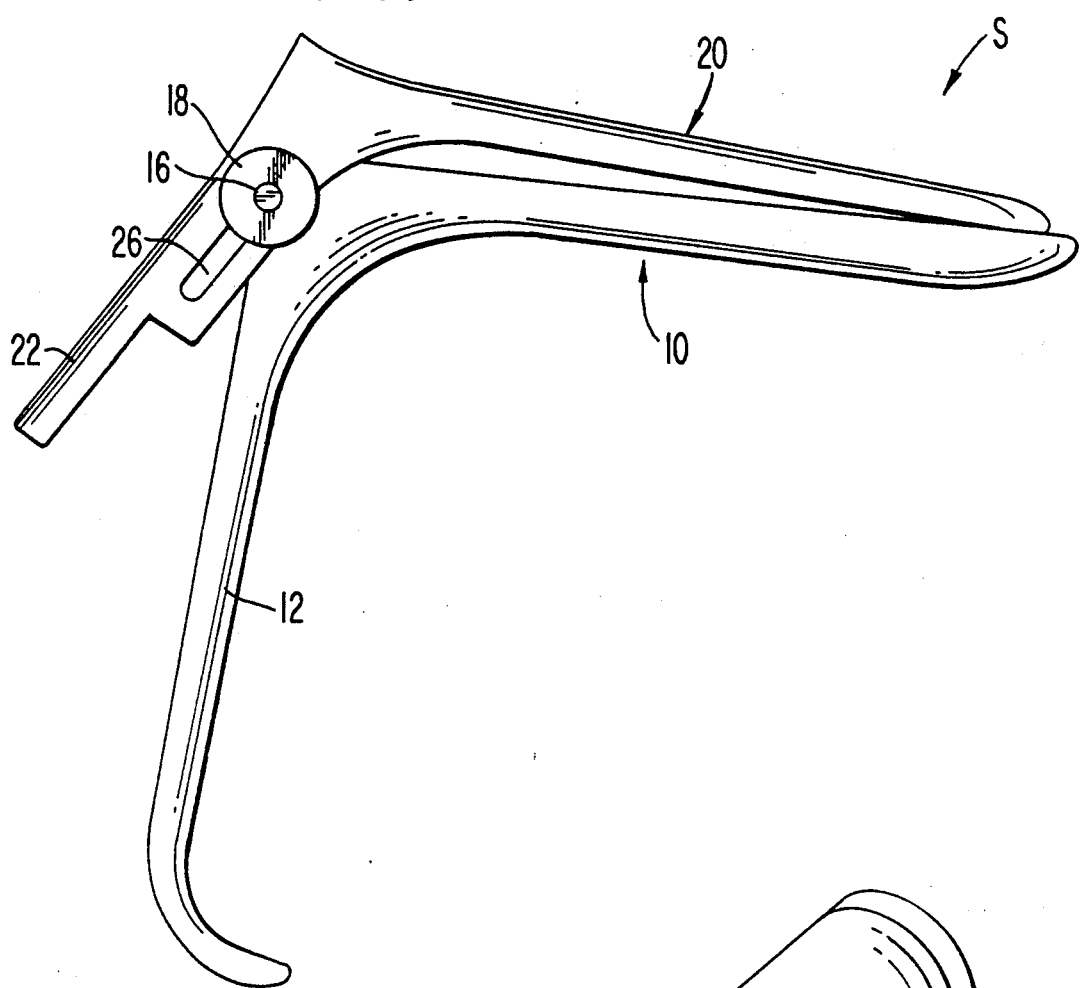
FIG. 1 is a right side view of a preferred embodiment of the speculum of the present invention.
Figure 4:
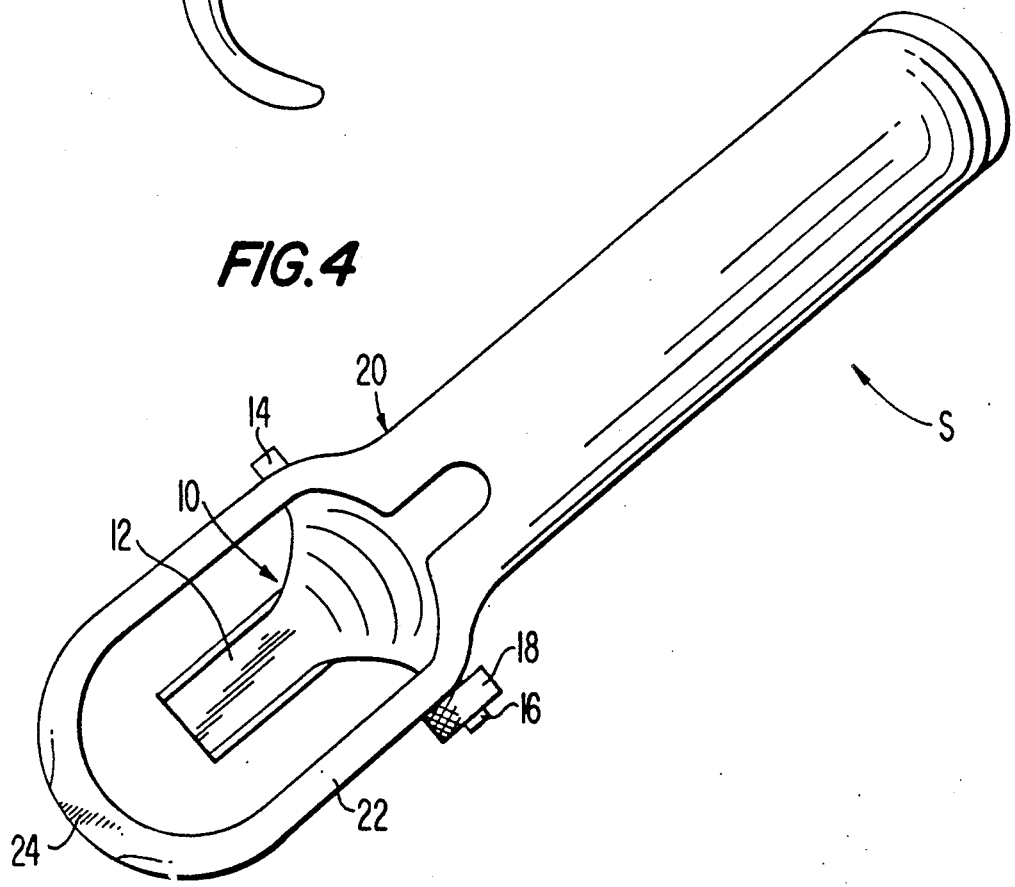
FIG. 4 is a top plan view of the speculum of FIG. 1.
Figure 2:
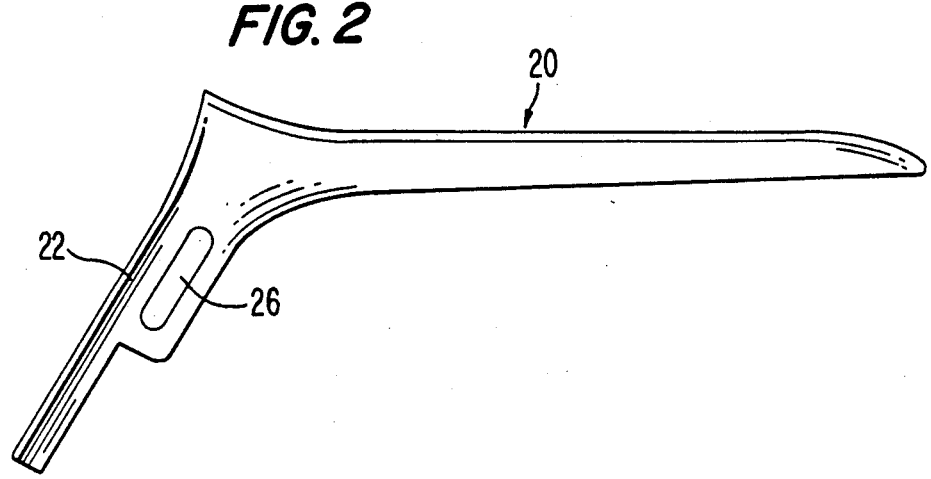
FIG. 2 is a right side view of the upper blade, showing a portion of the control mechanism.
Figure 3:
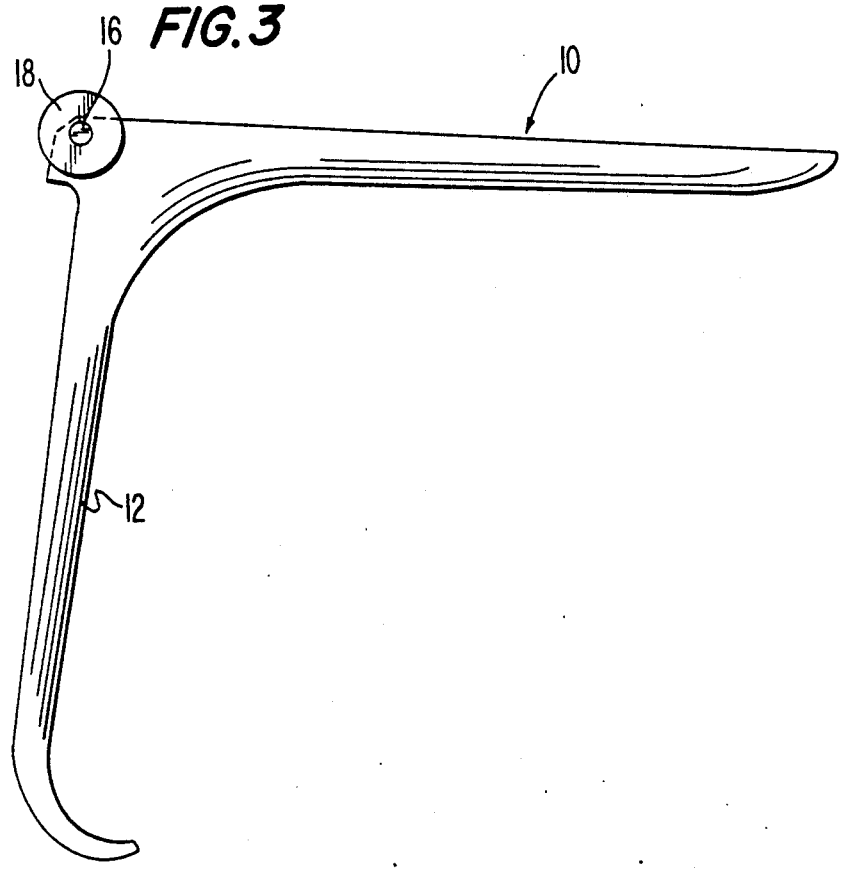
FIG. 3 is a right side view of the lower blade, showing another portion of the control mechanism.
Figure 7:
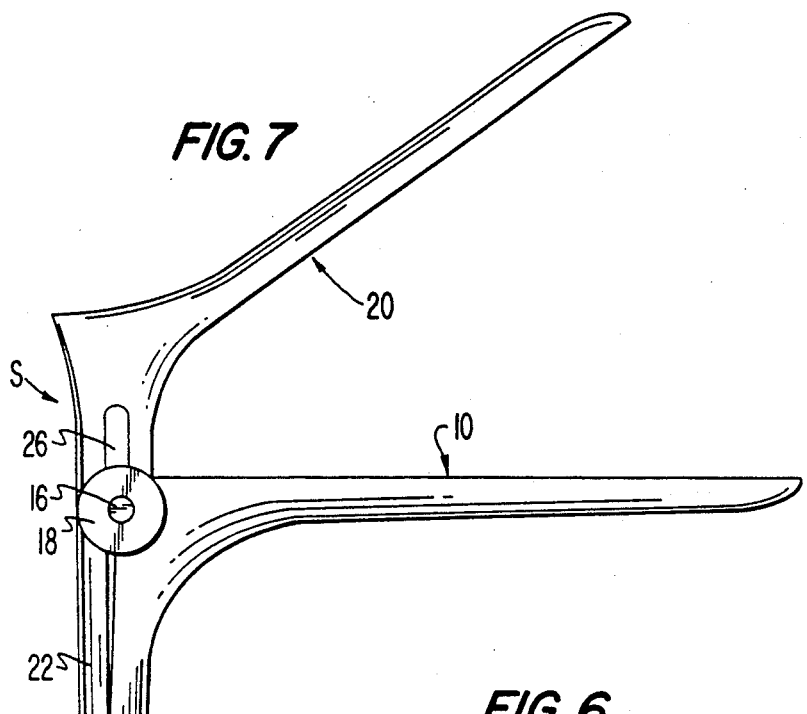
FIG. 7 is a right side view of the speculum with the blades at maximum angulation at the maximum aperture.
Figure 6:
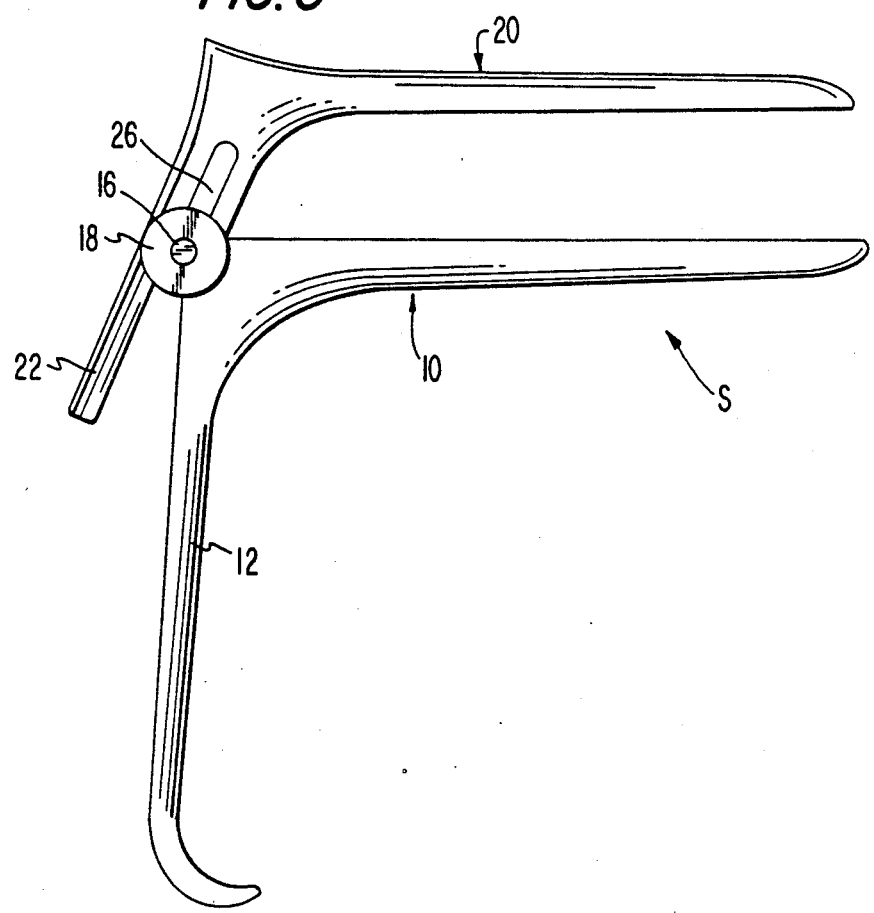
FIG. 6 is a right side view of the speculum with the blades parallel at the maximum aperture.

Referring now to the drawings, FIG. 1 shows a speculum S in accordance with a preferred embodiment of the invention. As shown in FIG. 1, the speculum includes a lower blade 10 having a depending rear handle portion 12 and an upper blade 20 having a depending rear handle portion 22. As is best seen in FIG. 4, the handle portion 22 of the upper blade is preferably U-shaped, and may have a centrally disposed thumb rest 24. The lower and upper blades 10 and 20 are shown separately in FIGS. 2 and 3, respectively.

In accordance with the present invention, lower and upper blades 10 and 12 of the speculum S are connected to one another by a control mechanism constituted by a unique pin, slot, and covering nut arrangement as will now be more particularly described. Referring to FIG. 4, the lower blade 10 is provided with two outwardly directed hinge pins 14 and 16 on its left-hand and right-hand sides, respectively, preferably near the junction of its depending handle portion 12 and its forwardly extending blade portion. See also FIG. 2. Each of the pins 14 and 16 is freely received in a corresponding one of a pair of slots formed in opposite sides of the handle portion 22 of the upper blade, the right-hand side slot 26 being seen in the drawings. A covering nut 16 is threadably received upon hinge pin 16 for locking and releasing of the blades relative to one another. When covering nut 18 is loosened, the upper blade is free to pivot and slide relative to the lower blade at the pin-slot connections, thus permitting individual or simultaneous adjustment of blade angulation and blade aperture. As will be readily understood from FIGS. 1 and 5–7, pivoting the handle portion of the upper blade about pins 14 and 16 changes blade angulation, whereas sliding the handle portion along the pins changes blade aperture. The desired configuration of the speculum may be obtained simply by applying thumb pressure in an appropriate manner to the upper blade handle 22, preferably at thumb rest 24. The blades may then be locked in the desired configuration simply by tightening the covering nut 18.

As will be appreciated from the foregoing description, the unique pin, slot, and covering nut arrangement of the invention requires the operation of only a single covering nut to lock and release the blades for both phases of speculum adjustment—that is, blade angulation and blade aperture. The arrangement further permits both phases of adjustment to be effected by the simple application of appropriate thumb pressure to the upper blade handle. The invention thus avoids the complex and tedious manipulations required by prior speculums.

Although a preferred embodiment of the invention has been described herein, it will be apparent to those skilled in the art that various modifications may be made without departing from the principles of the invention, the scope of which is defined in the appended claims.

I claim as my invention:

1. A vaginal speculum comprising an upper blade means and a lower blade means adapted for insertion into the vagina and having respective depending rear handles to enable holding and manipulation of the upper and lower blade means by a physician, a rear portion of said lower blade means having a pair of hinge pins respectively projecting outwardly from opposite right-hand and left-hand sides thereof and received in corresponding slots in opposite sides of the handle of said upper blade means such that the handle of said upper blade means may pivot on said hinge pins to adjust the angulation of said upper and lower blade means and may slide along said hinge pins to adjust the aperture of said upper and lower blade means, and a covering nut locking means axially threaded to one of said hinge pins for bearing against the handle of said upper blade means to lock said upper and lower blade means relative to each other simultaneously at the adjusted angulation and aperture.

2. A vaginal speculum according to claim 1, wherein said covering nut is threaded to the right-hand side hinge pin.

3. A vaginal speculum according to claim 1, wherein the handle of said upper blade means is U-shaped and has said slots respectively formed in opposite legs thereof.

4. A vaginal speculum according to claim 1, wherein said hinge pins are disposed near a junction of the handle of said lower blade means a forwardly extending blade portion of said lower blade means.

5. A vaginal speculum comprising an upper blade means and a lower blade means adapted for insertion into the vagina and having respective depending rear handles to enable holding and manipulation of the upper and lower blade means by a physician, said upper and lower blade means being coupled at right-hand sides and at left-hand sides thereof by respective pin-and-slot connection means for permitting said upper blade means to pivot relative to said lower blade means to adjust the angulation of said upper and lower blade means and for permitting said upper blade means to slide relative to said lower blade means to adjust the aperture of said upper and lower blade means, with a pin of one of said pin-and-slot connection means having a covering nut locking means axially threaded thereto for bearing against one of said upper and lower blade means to lock said upper and lower blade means relative to each other simultaneously at the adjusted angulation and aperture.

6. A vaginal speculum according to claim 5, wherein the handle of said upper blade means is U-shaped and has right-hand side and left-hand side legs each coupled to the handle of said lower blade means by a corresponding one of said pin-and-slot connection means.

7. A vaginal speculum according to claim 5, wherein each of said pin-and-slot connection means comprises an outwardly projecting pin disposed on said lower blade means and freely received in a slot formed in said upper blade means.

8. A vaginal speculum according to claim 7, wherein the handle of said upper blade means is U-shaped, and said slot of each said pin-and-slot connection means is formed in a corresponding leg of the U-shaped handle of said upper blade means.

* * * * *